United States Patent
Chang et al.

(10) Patent No.: US 12,083,077 B2
(45) Date of Patent: Sep. 10, 2024

(54) VAPORIZER MOUTHPIECE

(71) Applicant: JUUL Labs, Inc., San Francisco, CA (US)

(72) Inventors: Wei-Ling Chang, San Francisco, CA (US); Bryan White, San Francisco, CA (US); Kevin Lomeli, San Francisco, CA (US)

(73) Assignee: JUUL Labs, Inc., Washington, DC (US)

( * ) Notice: Subject to any disclaimer, the term of this patent is extended or adjusted under 35 U.S.C. 154(b) by 590 days.

(21) Appl. No.: 17/361,113

(22) Filed: Jun. 28, 2021

(65) Prior Publication Data

US 2021/0321668 A1    Oct. 21, 2021

Related U.S. Application Data

(63) Continuation of application No. PCT/US2019/068617, filed on Dec. 26, 2019.

(60) Provisional application No. 62/788,484, filed on Jan. 4, 2019.

(51) Int. Cl.
| | |
|---|---|
| *A24F 7/02* | (2006.01) |
| *A61K 9/00* | (2006.01) |
| *A61K 31/05* | (2006.01) |
| *A61K 31/352* | (2006.01) |
| *A61K 47/10* | (2017.01) |

(Continued)

(52) U.S. Cl.
CPC ............ *A61K 31/05* (2013.01); *A61K 9/0014* (2013.01); *A61K 31/352* (2013.01); *A61K 47/10* (2013.01); *A61K 47/38* (2013.01); *A24F 7/02* (2013.01); *A24F 40/485* (2020.01)

(58) Field of Classification Search
None
See application file for complete search history.

(56) References Cited

U.S. PATENT DOCUMENTS

| 6,196,232 B1 | 3/2001 | Chkadua |
| 9,078,475 B2 | 7/2015 | Li et al. |
| 9,198,466 B2 | 12/2015 | Liu |

(Continued)

FOREIGN PATENT DOCUMENTS

| EP | 3542654 B1 | 6/2021 |
| EP | 3542652 B1 | 9/2021 |

(Continued)

OTHER PUBLICATIONS

Anonymous (Mar. 19, 2017) "e-Cigarette tester "condoms"—package of 5", The Wayback Machine, Available online at: <http://web.archive.org/web/20170319220032/http://www.vaporkings.com:80/e-Cigarette-tester-condoms-package-of-5-p/ecig-testers.htm>, 4 pages.

*Primary Examiner* — Oscar C Jimenez
(74) *Attorney, Agent, or Firm* — Mintz, Levin, Cohn, Ferris, Glovsky and Popeo, P.C.

(57) ABSTRACT

A hygienic mouthpiece cover that is easily removed between sampling by users and is made from a recyclable biocompatible material is provided. Example embodiments of a mouthpiece cover includes an inlet, into which a vaporizer cartridge can be inserted, an outlet that a user draws vapor from, and a saliva transfer inhibitor that includes a guard physical barrier between the outlet and inlet to prevent saliva transfer to the cartridge, a saliva reservoir, and one or more draw holes of a number and size that vapor can pass through unrestricted.

20 Claims, 9 Drawing Sheets

(51) Int. Cl.
*A61K 47/38* (2006.01)
*A24F 40/485* (2020.01)

(56) References Cited

U.S. PATENT DOCUMENTS

| | | | |
|---|---|---|---|
| 9,345,269 B2 | 5/2016 | Liu | |
| 9,510,624 B2 | 12/2016 | Li et al. | |
| 9,730,471 B2 | 8/2017 | Li et al. | |
| 9,943,113 B2 | 4/2018 | Liu | |
| 10,244,793 B2 | 4/2019 | Monsees et al. | |
| 10,905,835 B2* | 2/2021 | Atkins | A24F 40/40 |
| 2011/0277780 A1 | 11/2011 | Terry et al. | |
| 2013/0074857 A1 | 3/2013 | Buchberger | |
| 2014/0174458 A1* | 6/2014 | Katz | A24F 1/00 |
| | | | 131/200 |
| 2015/0114406 A1 | 4/2015 | Newton | |
| 2015/0128970 A1 | 5/2015 | Liu | |
| 2015/0164143 A1 | 6/2015 | Maas | |
| 2015/0181928 A1 | 7/2015 | Liu | |
| 2015/0181941 A1 | 7/2015 | Liu | |
| 2015/0189920 A1 | 7/2015 | Liu | |
| 2015/0196055 A1 | 7/2015 | Liu | |
| 2015/0272211 A1 | 10/2015 | Chung | |
| 2015/0296886 A1 | 10/2015 | Li et al. | |
| 2016/0021933 A1 | 1/2016 | Thorens et al. | |
| 2016/0058072 A1 | 3/2016 | Liu | |
| 2016/0262459 A1 | 9/2016 | Monsees et al. | |
| 2016/0270442 A1 | 9/2016 | Liu | |
| 2016/0309785 A1* | 10/2016 | Holtz | H05B 3/06 |
| 2017/0333650 A1 | 11/2017 | Buchberger et al. | |
| 2017/0367407 A1* | 12/2017 | Althorpe | A24F 40/40 |
| 2018/0000156 A1 | 1/2018 | Qiu | |
| 2018/0140016 A1 | 5/2018 | Thorens | |
| 2018/0296777 A1 | 10/2018 | Terry et al. | |
| 2018/0310625 A1* | 11/2018 | Alarcon | H05B 3/03 |
| 2019/0014825 A1 | 1/2019 | Saygili | |
| 2020/0288770 A1* | 9/2020 | Potter | A24F 40/30 |
| 2020/0324066 A1* | 10/2020 | Potter | H04L 12/10 |
| 2021/0000177 A1* | 1/2021 | Novak, III | H05B 1/0244 |
| 2021/0030073 A1* | 2/2021 | Yang | A24B 15/167 |
| 2022/0007719 A1* | 1/2022 | Potter | A24F 40/42 |
| 2022/0175041 A1* | 6/2022 | Liu | A24F 40/485 |
| 2022/0232891 A1* | 7/2022 | Potter | A24F 40/70 |
| 2022/0287377 A1* | 9/2022 | Matsuda | A24F 40/30 |
| 2023/0020470 A1* | 1/2023 | Johnson | A24F 40/10 |
| 2023/0172280 A1* | 6/2023 | Israel | A24F 40/10 |
| | | | 131/329 |

FOREIGN PATENT DOCUMENTS

| | | |
|---|---|---|
| EP | 3666097 B1 | 12/2021 |
| EP | 3666099 B1 | 1/2022 |
| EP | 3669680 B1 | 3/2022 |
| KR | 10-2015-0000417 A | 1/2015 |
| WO | WO-2013110208 A1 | 8/2013 |
| WO | WO-2013110209 A1 | 8/2013 |
| WO | WO-2013110210 A1 | 8/2013 |
| WO | WO-2015120588 A1 | 8/2015 |
| WO | WO-2015188296 A1 | 12/2015 |
| WO | WO-2016127287 A1 | 8/2016 |
| WO | WO-2017092144 A1 | 6/2017 |
| WO | WO-2017205838 A1 | 11/2017 |
| WO | WO-2018165769 A1 | 9/2018 |

* cited by examiner

SECTION A-A

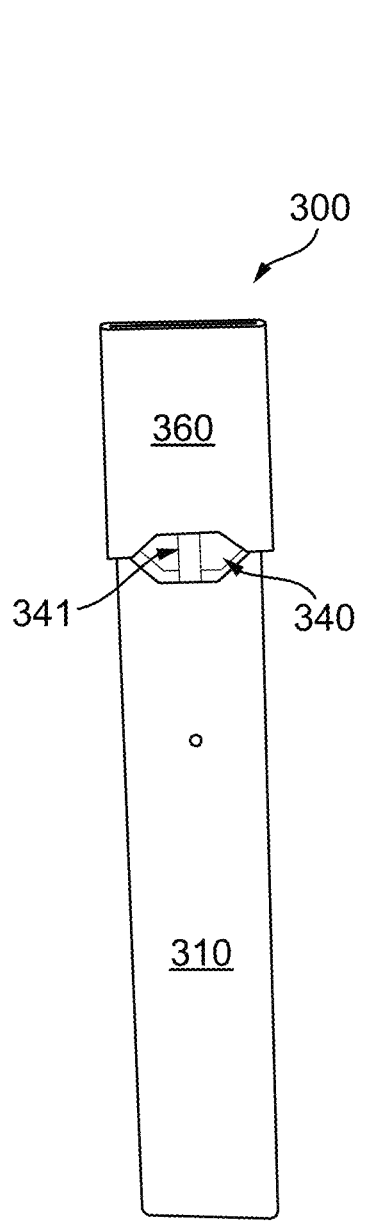
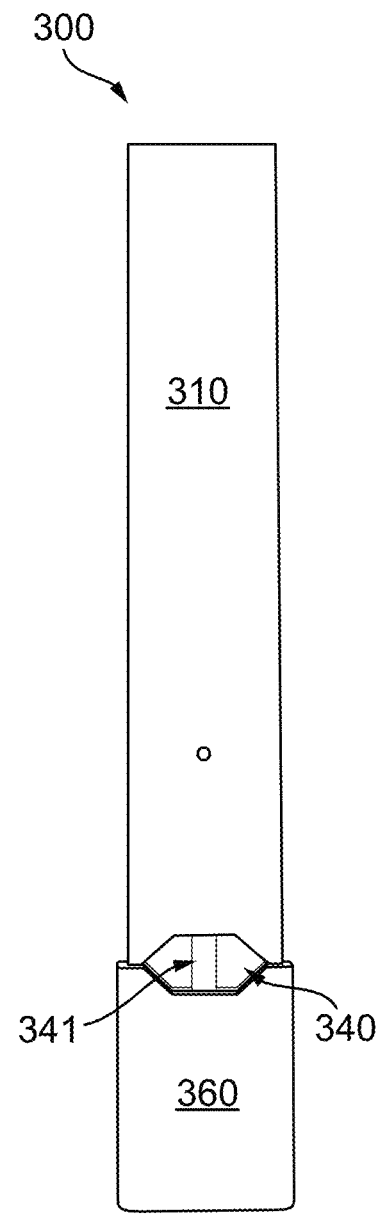
FIG. 3A     FIG. 3B

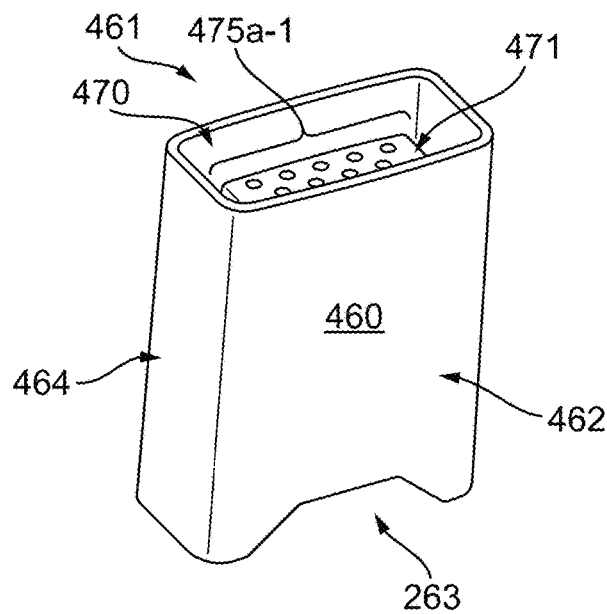
FIG. 4
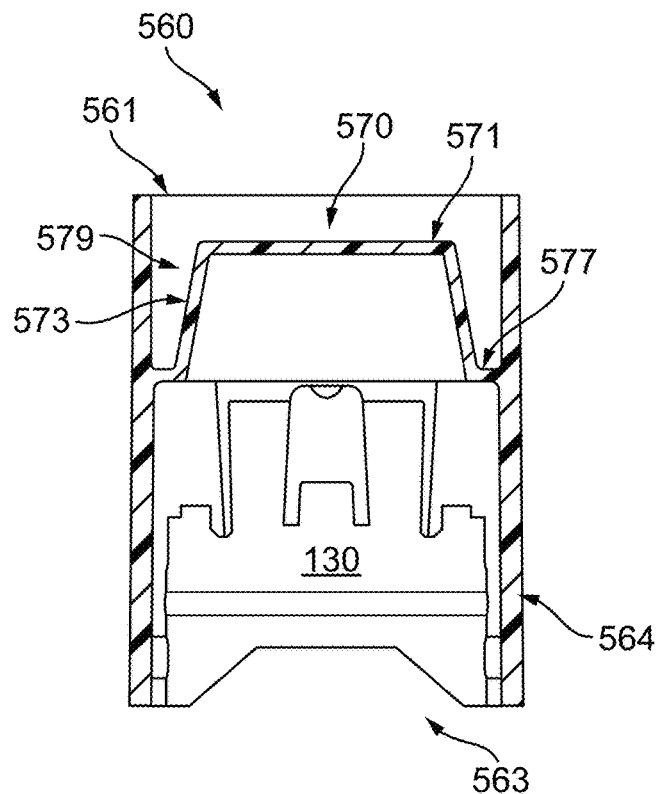 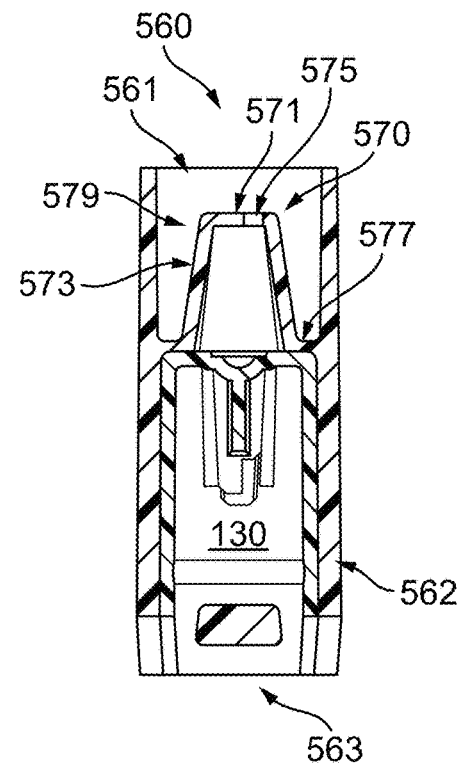
FIG. 5A  FIG. 5B

VAPORIZER MOUTHPIECE

CROSS-REFERENCE TO RELATED APPLICATIONS

The present application is a bypass continuation under 35 U.S.C. § 120 and claims priority to PCT/US19/68617 (US2019068617 W), filed on Dec. 26, 2019, which claims the benefit, under 35 U.S.C. § 119(e), of the earlier filing date of U.S. Provisional Patent Application Ser. No. 62/788,484 (US201962788484P), filed on Jan. 4, 2019, the content of each of the above applications is incorporated by reference herein in entirety.

FIELD

The subject matter described herein relates to vaporizer devices, disposable vaporizer cartridges, and vaporizer mouthpiece covers.

BACKGROUND

Vaporizer devices, which can also be referred to as vaporizers, electronic vaporizer devices or e-vaporizer devices, can be used to deliver an aerosol (or "vapor") containing one or more active ingredients through inhalation of the aerosol by a user of the vaporizing device. For example, electronic cigarettes, which may also be referred to as e-cigarettes, are a class of vaporizer devices that are typically battery powered and that may be used to simulate the experience of cigarette smoking, but without burning of tobacco or other substances.

In use of a vaporizer device, the user inhales an aerosol, commonly called vapor, which may be generated by a heating element that vaporizes (which generally refers to causing a liquid or solid to at least partially transition to the gas phase) a vaporizable material, which may be liquid, a solution, a solid, a wax, or any other form as may be compatible with use of a specific vaporizer device. The vaporizable material used with a vaporizer can be provided within a cartridge (e.g., a part of the vaporizer that contains the vaporizable material in a reservoir) that includes a mouthpiece (e.g., for inhalation by a user).

To receive the inhalable aerosol generated by a vaporizer device, a user may, in certain examples, activate the vaporizer device by taking a puff, by pressing a button, or by some other approach. A puff, as the term is generally used (and also used herein), refers to inhalation by the user in a manner that causes a volume of air to be drawn into the vaporizer device such that the inhalable aerosol is generated by a combination of vaporized vaporizable material with the air.

Inhalation by the user is typically performed by placing a mouthpiece or mouthpiece cover of the vaporizer to the user's mouth and then inhaling in a manner that causes a volume of air to be drawn into the vaporizer device and a combination of vaporized vaporizable material and air to exit the device into the user's mouth and airway.

A typical approach by which a vaporizer device generates an inhalable aerosol from a vaporizable material involves heating the vaporizable material in a vaporization chamber (or a heater chamber) to cause the vaporizable material to be converted to the gas (or vapor) phase. A vaporization chamber generally refers to an area or volume in the vaporizer device within which a heat source (e.g., conductive, convective, and/or radiative) causes heating of a vaporizable material to produce a mixture of air and vaporized vaporizable material for inhalation by a user of the vaporization device.

In some vaporizer device embodiments, the vaporizable material can be drawn out of a reservoir and into the vaporization chamber via a wicking element (a wick). Such drawing of the vaporizable material into the vaporization chamber can be due, at least in part, to capillary action provided by the wick, which pulls the vaporizable material along the wick in the direction of the vaporization chamber. However, as vaporizable material is drawn out of the reservoir, the pressure inside the reservoir is reduced, thereby creating a vacuum and acting against the capillary action. This can reduce the effectiveness of the wick to draw the vaporizable material into the vaporization chamber, thereby reducing the effectiveness of the vaporization device to vaporize a desired amount of vaporizable material when, for example, a user takes a puff on the vaporizer device. Furthermore, the vacuum created in the reservoir can ultimately result in the inability to draw all of the vaporizable material into the vaporization chamber, thereby wasting vaporizable material. As such, improved vaporization devices and/or vaporization cartridges that improve upon or overcome these issues is desired.

The term vaporizer device, as used herein consistent with the current subject matter, generally refers to portable, self-contained, devices that are convenient for personal use. Typically, such devices are controlled by one or more switches, buttons, touch sensitive devices, or other user input functionality or the like (which can be referred to generally as controls) on the vaporizer, although a number of devices that may wirelessly communicate with an external controller (e.g., a smartphone, a smart watch, other wearable electronic devices, etc.) have recently become available. Control, in this context, refers generally to an ability to influence one or more of a variety of operating parameters, which may include without limitation any of causing the heater to be turned on and/or off, adjusting a minimum and/or maximum temperature to which the heater is heated during operation, various games or other interactive features that a user might access on a device, and/or other operations.

Various vaporizable materials having a variety of contents and proportions of such contents can be contained in the cartridge. Some vaporizable materials, for example, may have a smaller percentage of active ingredients per total volume of vaporizable material, such as due to regulations requiring certain active ingredient percentages. As such, a user may need to vaporize a large amount of vaporizable material (e.g., compared to the overall volume of vaporizable material that can be stored in a cartridge) to achieve a desired effect.

The variety of contents and proportions of such contents can include not only certain active ingredients but also inactive ingredients that provide flavoring to enhance the user experience. As vaporization devices gain popularity as an alternative to traditional cigarettes, interested smokers or vaporizer users desire to try samples of vaporizers and vaporizable materials at trade shows, events, and retail stores. Users often want to sample the different types of cartridges containing the various vaporizable materials prior to purchasing a particular cartridge type. Cartridges are generally designed and manufactured with an amount of vaporizable material that is adequate for multiple puffs, for example about 200 puffs. Therefore, multiple users often sample from the same trial cartridge. The currently available mouthpiece covers enable sampling in sanitary manner but offer a poor user experience at best.

SUMMARY

Example embodiments of a mouthpiece cover for a vaporizer device are presented herein. The mouthpiece cover includes an outlet for vapor to exit the vaporizer, an inlet arranged at a distal end from the outlet, and configured to sheathe a vaporizer cartridge mouthpiece. The vaporizer cartridge mouthpiece may be held within the mouthpiece cover by a first retention force. The vaporizer cartridge connected to the mouthpiece may be held within a vaporizer cartridge receptacle by a second retention force. The first retention force may be less than the second retention force to allow for the mouthpiece cover to be removed from the mouthpiece without forcing the cartridge out of the cartridge receptacle. The mouthpiece cover can be made from a recyclable material, food grade material, biocompatible material, or any combination thereof, such as a food grade polypropylene. The mouthpiece cover can be arranged as a generally rounded rectangular tube having two longs sides in parallel and orthogonal to two short sides, wherein the long sides are in an offset arrangement with the vaporizer cartridge mouthpiece. The offset may be approximately 0.05 mm from the pod. This offset enables the mouthpiece cover to fit over vaporizer pods on the highest and lowest ends of the range of manufacturing tolerances.

Example embodiments of the mouthpiece cover include a saliva transfer inhibitor and/or guard arranged between the outlet and the inlet, and configured to obstruct the vaporizer cartridge mouthpiece from coupling to the outlet, and a reservoir for capturing saliva, the reservoir defined by a void between the outlet and the inhibitor/guard. This reservoir captures and prevents saliva from transferring into the pod mouthpiece. Example embodiments of the mouthpiece cover include more than one draw hole in the inhibitor/guard, the more than one draw hole configured for vapor to pass through the guard. In an example embodiment, this is achieved by nine (9) 0.8 mm diameter holes. The number and size of the holes enables vapor to pass through, while preventing saliva transfer into the pod. Data shows that the example embodiment adds only 2 millimeters per water column (mmwc) draw restriction to the vaporizer system. The inhibitor/guard can be arranged as a generally rectangular pyramidal frustum with the bottom open to the vaporizer cartridge mouthpiece and the top proximate to the outlet.

The fit of an example embodiment of the mouthpiece cover over the pod is designed so that the mouthpiece cover retention force is less than the pod retention force. This means the mouthpiece cover can be easily removed without also removing the pod from the device, and without causing pod leakage or damage. The fit also enables the mouthpiece cover to stay on securely, such that when only the mouthpiece is held, the device still remains attached. Likewise, when only the device is held, the mouthpiece remains attached.

Example embodiments of the mouthpiece cover can be designed so that the user can remove the cover and the pod at the same time, by lightly pinching the long sides upon removal. This is achieved by offsetting the long sides of mouthpiece cover by approximately 0.05 mm from the pod. This offset also enables the mouthpiece cover to fit over pods on the highest and lowest ends of the tolerance range. Because example embodiments of the mouthpiece cover fit over the entire pod mouthpiece, this full coverage provides increased sanitation.

In accordance with some embodiments, a vaporizer device accessory is provided that includes a body having a hollow interior to fit over a mouthpiece of a vaporize device. The body may include an outlet on a first side of the body; an inlet on a second side of the body opposite to the outlet, the inlet having been formed to receive therein a distal end of the mouthpiece; and a saliva transfer inhibitor comprising a guard with draw holes positioned between the outlet and the inlet, the saliva transfer inhibitor shaped as a pyramidal frustum. A base of the pyramidal frustum is coupled to an interior of the rectangular tube mouthpiece cover through a guard lip, in one example, and may be substantially rectangular in shape. Depending on implementation, the guard lip acts as an obstruction, engaging with a mouthpiece portion of the vaporizer device cartridge to stop the cartridge from insertion into the body beyond a first threshold.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

These and other aspects, features and advantages of various implementations will be apparent from the following more particular description of example embodiments of the invention, as illustrated in the accompanying drawings in which like reference characters refer to the same parts throughout the different views. The accompanying drawings, which are incorporated in and constitute a part of this specification, show certain aspects of the subject matter disclosed herein and, together with the description, help explain some of the principles associated with the disclosed implementations. The drawings are not necessarily to scale, emphasis instead being placed upon illustrating embodiments of the present invention. In the drawings:

FIGS. 3A and 3B illustrate retention forces associated with the coupling of an example embodiment of a vaporizer mouthpiece cover device and a vaporizer device in accordance with the implementations of the current subject matter;

FIG. 4 is a further isometric view of an outlet of an example embodiment of a vaporizer mouthpiece cover device in accordance with the implementations of the current subject matter;

FIGS. 5A and 5B are further cross-sectional views of an example embodiment of a vaporizer mouthpiece cover device in accordance with the implementations of the current subject matter;

When practical, similar reference numbers denote similar structures, features, or elements.

DETAILED DESCRIPTION OF EXAMPLE EMBODIMENTS

Figure 1A:
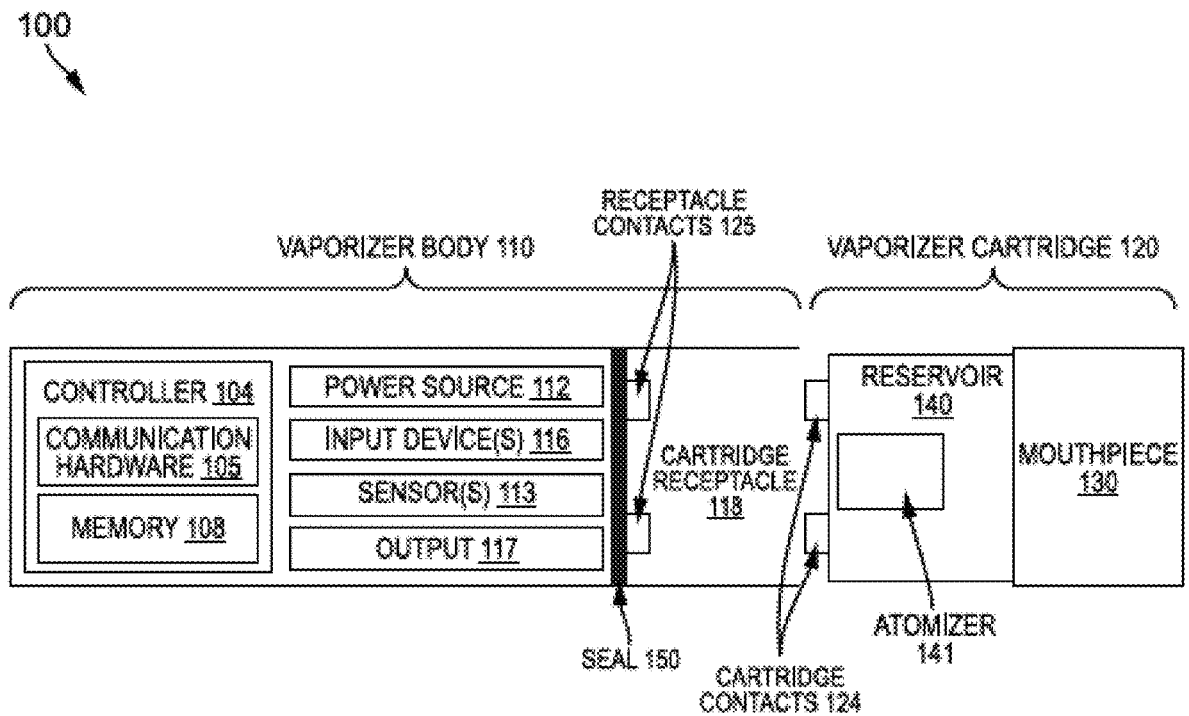
FIG. 1A illustrates a block diagram of a vaporizer.

Implementations of the current subject matter include devices relating to vaporizing one or more materials for inhalation by a user. More particularly, implementation of the current subject matter include removable and saliva transfer inhibiting mouthpiece devices and combinations thereof. The term "vaporizer" is used generically in the following description to refer to a vaporizer device. Examples of vaporizers consistent with implementations of the current subject matter include electronic vaporizers, electronic cigarettes, e-cigarettes, or the like. Such vaporizers are generally portable, hand-held devices that heat a vaporizable material to provide an inhalable dose of the material.

The vaporizable material used with a vaporizer may optionally be provided within a cartridge (e.g., a part of the vaporizer that contains the vaporizable material in a reservoir or other container and that can be refillable when empty or disposable in favor of a new cartridge containing additional vaporizable material of a same or different type). A vaporizer may be a cartridge-using vaporizer, a cartridge-less vaporizer, or a multi-use vaporizer capable of use with or without a cartridge. For example, a multi-use vaporizer may include a heating chamber (e.g., an oven) configured to receive a vaporizable material directly in the heating chamber and also to receive a cartridge or other replaceable device having a reservoir, a volume, or the like for at least partially containing a usable amount of vaporizable material. Herein, the term "pod" is synonymous and may be used interchangeably with the term "cartridge."

In various implementations, a vaporizer may be configured for use with liquid vaporizable material (e.g., a carrier solution in which an active and/or inactive ingredient(s) are suspended or held in solution or a neat liquid form of the vaporizable material itself) or a solid vaporizable material. A solid vaporizable material may include a plant material that emits some part of the plant material as the vaporizable material (e.g., such that some part of the plant material remains as waste after the vaporizable material is emitted for inhalation by a user) or optionally can be a solid form of the vaporizable material itself (e.g., a "wax") such that all of the solid material can eventually be vaporized for inhalation. A liquid vaporizable material can likewise be capable of being completely vaporized or can include some part of the liquid material that remains after all of the material suitable for inhalation has been consumed.

A variety of vaporizable materials are currently commercially available. These commercially available vaporizable materials come in a variety of contents and proportions of such contents including active and inactive ingredients such as flavorings to enhance the user experience. Users often want to sample the different varieties of vaporizable materials prior to purchasing a particular type. Trade shows, events, and retail stores often host trials so that interested users can sample the different types of vaporizable materials available to aid the users' purchasing decision.

Commercially available cartridges containing the vaporizable material are generally designed and manufactured to hold an amount of vaporizable material that is adequate for multiple puffs, for example about 200 puffs. Therefore, at most trials sample cartridges are available for multiple users to sample from. That is, multiple interested users sample a puff(s) from the same trial cartridge. When multiple users are sampling from the same trial cartridge it is important that sampling be done in a sanitary manner.

The prior art mouthpieces include a mouthpiece device made of silicone rubber that has one large hole for vapor to pass through. While the prior art mouthpiece allows multiple users to sample the same trial cartridge in a sanitary manner, the user experience with the prior art mouthpiece devices is poor. That poor user experience can undercut the reason for offering a trial in the first place, that is to facilitate a purchase by an interested user. A poor user experience can also damage a manufacturer's brand, and possibly put-off retailers and others from offering samples due to the hassle.

The prior art mouthpiece devices suffer from a number of drawbacks. The prior art devices can affect the draw, reduce airflow and cause vapor to get trapped between the mouthpiece cover and cartridge (or pod). The prior art mouthpiece devices suffer from a poor cover removal experience. Removing the mouthpiece cover from the pod is very difficult, takes several minutes, and causes the user to struggle. Often, small tools are need to facilitate the removal. The difficulty can and often does result in a damaged pod. During the removal process, the pod often becomes stuck inside the mouthpiece cover. In order to remove the pod, the user must squeeze mouthpiece and pod very tightly. This often results in a damaged pod and leakage all over a user's or retailer's hands.

Further, the prior art mouthpiece devices suffer from sanitary deficiencies. The prior art mouthpiece devices do not effectively retain saliva, increasing the possibility of saliva being transferred to the cartridge and defeating the purpose of the cover. The prior art mouthpiece devices also do not fully cover the pod mouthpiece, allowing for the possibility of saliva being transferred to the cartridge and defeating the purpose of the cover. The prior art mouthpiece cover is made from silicone rubber, which is a non-recyclable material and non-biodegradable. The use of silicone rubber for mouthpiece covers can lead to the buildup of used covers, which may negatively impact the environment and adversely affect brand commitment to sustainability, and be frustrating to retailers.

Example embodiments of the subject matter described herein address the problem discussed above.

Referring to the block diagram of FIG. 1A, a vaporizer 100 typically includes a power source 112 (such as a battery which may be a rechargeable battery), and a controller 104 (e.g., a processor, circuitry, etc. capable of executing logic) for controlling delivery of heat to an atomizer 141 to cause a vaporizable material to be converted from a condensed form (e.g., a solid, a liquid, a solution, a suspension, a part of an at least partially unprocessed plant material, etc.) to the gas phase. The controller 104 may be part of one or more printed circuit boards (PCBs) consistent with certain implementations of the current subject matter.

After conversion of the vaporizable material to the gas phase, and depending on the type of vaporizer, the physical and chemical properties of the vaporizable material, and/or other factors, at least some of the gas-phase vaporizable material may condense to form particulate matter in at least a partial local equilibrium with the gas phase as part of an aerosol, which can form some or all of an inhalable dose provided by the vaporizer 100 for a given puff or draw on the vaporizer. It will be understood that the interplay between gas and condensed phases in an aerosol generated by a vaporizer can be complex and dynamic, as factors such as ambient temperature, relative humidity, chemistry, flow conditions in airflow paths (both inside the vaporizer and in the airways of a human or other animal), mixing of the gas-phase or aerosol-phase vaporizable material with other air streams, etc. may affect one or more physical parameters of an aerosol. In some vaporizers, and particularly for vaporizers for delivery of more volatile vaporizable materials, the inhalable dose may exist predominantly in the gas phase (i.e., formation of condensed phase particles may be very limited).

Vaporizers for use with liquid vaporizable materials (e.g., neat liquids, suspensions, solutions, mixtures, etc.) typically include an atomizer 141 in which a wicking element (also referred to herein as a wick (not shown in FIG. 1A), which can include any material capable of causing fluid motion by capillary pressure) conveys an amount of a liquid vaporizable material to a part of the atomizer that includes a heating element (also not shown in FIG. 1A). The wicking element is generally configured to draw liquid vaporizable material from a reservoir configured to contain (and that may in use contain) the liquid vaporizable material such that the liquid vaporizable material may be vaporized by heat delivered from a heating element. The wicking element may also optionally allow air to enter the reservoir to replace the volume of liquid removed. In other words, capillary action pulls liquid vaporizable material into the wick for vaporization by the heating element (described below), and air may, in some implementations of the current subject matter, return to the reservoir through the wick to at least partially equalize pressure in the reservoir. Other approaches to allowing air back into the reservoir to equalize pressure are also within the scope of the current subject matter.

The heating element can be or include one or more of a conductive heater, a radiative heater, and a convective heater. One type of heating element is a resistive heating element, which can be constructed of or at least include a material (e.g., a metal or alloy, for example a nickel-chromium alloy, or a non-metallic resistor) configured to dissipate electrical power in the form of heat when electrical current is passed through one or more resistive segments of the heating element. In some implementations of the current subject matter, an atomizer can include a heating element that includes a resistive coil or other heating element wrapped around, positioned within, integrated into a bulk shape of, pressed into thermal contact with, or otherwise arranged to deliver heat to a wicking element to cause a liquid vaporizable material drawn by the wicking element from a reservoir to be vaporized for subsequent inhalation by a user in a gas and/or a condensed (e.g., aerosol particles or droplets) phase. Other wicking element, heating element, and/or atomizer assembly configurations are also possible, as discussed further below.

Certain vaporizers may also or alternatively be configured to create an inhalable dose of gas-phase and/or aerosol-phase vaporizable material via heating of a non-liquid vaporizable material, such as for example a solid-phase vaporizable material (e.g., a wax or the like) or plant material (e.g., tobacco leaves and/or parts of tobacco leaves) containing the vaporizable material. In such vaporizers, a resistive heating element may be part of or otherwise incorporated into or in thermal contact with the walls of an oven or other heating chamber into which the non-liquid vaporizable material is placed. Alternatively, a resistive heating element or elements may be used to heat air passing through or past the non-liquid vaporizable material to cause convective heating of the non-liquid vaporizable material. In still other examples, a resistive heating element or elements may be disposed in intimate contact with plant material such that direct conductive heating of the plant material occurs from within a mass of the plant material (e.g., as opposed to only by conduction inward form walls of an oven).

The heating element may be activated (e.g., a controller, which is optionally part of a vaporizer body as discussed below, may cause current to pass from the power source through a circuit including the resistive heating element, which is optionally part of a vaporizer cartridge as discussed below), in association with a user puffing (e.g., drawing, inhaling, etc.) on a mouthpiece 130 of the vaporizer to cause air to flow from an air inlet, along an airflow path that passes an atomizer (e.g., wicking element and heating element), optionally through one or more condensation areas or chambers, to an air outlet in the mouthpiece. Incoming air passing along the airflow path passes over, through, etc. the atomizer, where gas phase vaporizable material is entrained into the air. As noted above, the entrained gas-phase vaporizable material may condense as it passes through the remainder of the airflow path such that an inhalable dose of the vaporizable material in an aerosol form can be delivered from the air outlet (e.g., in a mouthpiece 130 for inhalation by a user).

Activation of the heating element may be caused by automatic detection of the puff based on one or more of signals generated by one or more sensors 113, such as for example a pressure sensor or sensors disposed to detect pressure along the airflow path relative to ambient pressure (or optionally to measure changes in absolute pressure), one or more motion sensors of the vaporizer, one or more flow sensors of the vaporizer, a capacitive lip sensor of the vaporizer; in response to detection of interaction of a user with one or more input devices 116 (e.g., buttons or other tactile control devices of the vaporizer 100), receipt of signals from a computing device in communication with the vaporizer; and/or via other approaches for determining that a puff is occurring or imminent.

As alluded to in the previous paragraph, a vaporizer consistent with implementations of the current subject matter may be configured to connect (e.g., wirelessly or via a wired connection) to a computing device (or optionally two or more devices) in communication with the vaporizer. To this end, the controller 104 may include communication hardware 105. The controller 104 may also include a memory 108. A computing device can be a component of a vaporizer system that also includes the vaporizer 100, and can include its own communication hardware, which can establish a wireless communication channel with the communication hardware 105 of the vaporizer 100. For example, a computing device used as part of a vaporizer system may include a general-purpose computing device (e.g., a smartphone, a tablet, a personal computer, some other portable device such as a smartwatch, or the like) that executes software to produce a user interface for enabling a user of the device to interact with a vaporizer. In other implementations of the current subject matter, such a device used as part of a vaporizer system can be a dedicated piece of hardware such as a remote control or other wireless or wired device having one or more physical or soft (e.g., configurable on a screen or other display device and selectable via user interaction with a touch-sensitive screen or some other input device like a mouse, pointer, trackball, cursor buttons, or the like) interface controls. The vaporizer can also include one or more output 117 features or devices for providing information to the user.

A computing device that is part of a vaporizer system as defined above can be used for any of one or more functions, such as controlling dosing (e.g., dose monitoring, dose setting, dose limiting, user tracking, etc.), controlling sessioning (e.g., session monitoring, session setting, session limiting, user tracking, etc.), controlling nicotine delivery (e.g., switching between nicotine and non-nicotine vaporizable material, adjusting an amount of nicotine delivered, etc.), obtaining locational information (e.g., location of other users, retailer/commercial venue locations, vaping locations, relative or absolute location of the vaporizer itself, etc.), vaporizer personalization (e.g., naming the vaporizer, locking/password protecting the vaporizer, adjusting one or more parental controls, associating the vaporizer with a user group, registering the vaporizer with a manufacturer or warranty maintenance organization, etc.), engaging in social activities (e.g., games, social media communications, interacting with one or more groups, etc.) with other users, or the like. The terms "sessioning", "session", "vaporizer session," or "vapor session," are used generically to refer to a period devoted to the use of the vaporizer. The period can include a time period, a number of doses, an amount of vaporizable material, and/or the like.

In the example in which a computing device provides signals related to activation of the resistive heating element, or in other examples of coupling of a computing device with a vaporizer for implementation of various control or other functions, the computing device executes one or more computer instructions sets to provide a user interface and underlying data handling. In one example, detection by the computing device of user interaction with one or more user interface elements can cause the computing device to signal the vaporizer 100 to activate the heating element, either to a full operating temperature for creation of an inhalable dose of vapor/aerosol. Other functions of the vaporizer may be controlled by interaction of a user with a user interface on a computing device in communication with the vaporizer.

The temperature of a resistive heating element of a vaporizer may depend on a number of factors, including an amount of electrical power delivered to the resistive heating element and/or a duty cycle at which the electrical power is delivered, conductive heat transfer to other parts of the electronic vaporizer and/or to the environment, latent heat losses due to vaporization of a vaporizable material from the wicking element and/or the atomizer as a whole, and convective heat losses due to airflow (e.g., air moving across the heating element or the atomizer as a whole when a user inhales on the electronic vaporizer). As noted above, to reliably activate the heating element or heat the heating element to a desired temperature, a vaporizer may, in some implementations of the current subject matter, make use of signals from a pressure sensor to determine when a user is inhaling. The pressure sensor can be positioned in the airflow path and/or can be connected (e.g., by a passageway or other path) to an airflow path connecting an inlet for air to enter the device and an outlet via which the user inhales the resulting vapor and/or aerosol such that the pressure sensor experiences pressure changes concurrently with air passing through the vaporizer device from the air inlet to the air outlet. In some implementations of the current subject matter, the heating element may be activated in association with a user's puff, for example by automatic detection of the puff, for example by the pressure sensor detecting a pressure change in the airflow path.

Typically, the pressure sensor (as well as any other sensors 113) can be positioned on or coupled (e.g., electrically or electronically connected, either physically or via a wireless connection) to the controller 104 (e.g., a printed circuit board assembly or other type of circuit board). To take measurements accurately and maintain durability of the vaporizer, it can be beneficial to provide a resilient seal 150 to separate an airflow path from other parts of the vaporizer. The seal 150, which can be a gasket, may be configured to at least partially surround the pressure sensor such that connections of the pressure sensor to internal circuitry of the vaporizer are separated from a part of the pressure sensor exposed to the airflow path. In an example of a cartridge-based vaporizer, the seal 150 may also separate parts of one or more electrical connections between a vaporizer body 110 and a vaporizer cartridge 120. Such arrangements of a seal 150 in a vaporizer 100 can be helpful in mitigating against potentially disruptive impacts on vaporizer components resulting from interactions with environmental factors such as water in the vapor or liquid phases, other fluids such as the vaporizable material, etc. and/or to reduce escape of air from the designed airflow path in the vaporizer. Unwanted air, liquid or other fluid passing and/or contacting circuitry of the vaporizer can cause various unwanted effects, such as alter pressure readings, and/or can result in the buildup of unwanted material, such as moisture, the vaporizable material, etc. in parts of the vaporizer where they may result in poor pressure signal, degradation of the pressure sensor or other components, and/or a shorter life of the vaporizer. Leaks in the seal 150 can also result in a user inhaling air that has passed over parts of the vaporizer device containing or constructed of materials that may not be desirable to be inhaled.

A general class of vaporizers that have recently gained popularity includes a vaporizer body 110 that includes a controller 104, a power source 112 (e.g., battery), one more sensors 113, charging contacts, a seal 150, and a cartridge receptacle 118 configured to receive a vaporizer cartridge 120 for coupling with the vaporizer body through one or more of a variety of attachment structures. In some examples, vaporizer cartridge 120 includes a reservoir 140 for containing a liquid vaporizable material and a mouthpiece 130 for delivering an inhalable dose to a user. The vaporizer cartridge can include an atomizer 141 having a wicking element and a heating element, or alternatively, one or both of the wicking element and the heating element can be part of the vaporizer body. In implementations in which any part of the atomizer 141 (e.g., heating element and/or wicking element) is part of the vaporizer body, the vaporizer can be configured to supply liquid vaporizer material from a reservoir in the vaporizer cartridge to the atomizer part(s) included in the vaporizer body.

Cartridge-based configurations for vaporizers that generate an inhalable dose of a non-liquid vaporizable material via heating of a non-liquid vaporizable material are also within the scope of the current subject matter. For example, a vaporizer cartridge may include a mass of plant material that is processed and formed to have direct contact with parts of one or more resistive heating elements, and such a vaporizer cartridge may be configured to be coupled mechanically and electrically to a vaporizer body that includes a processor, a power source, and electrical contacts for connecting to corresponding cartridge contacts for completing a circuit with the one or more resistive heating elements.

In vaporizers in which the power source 112 is part of a vaporizer body 110 and a heating element is disposed in a vaporizer cartridge 120 configured to couple with the vaporizer body 110, the vaporizer 100 may include electrical connection features (e.g., means for completing a circuit) for completing a circuit that includes the controller 104 (e.g., a printed circuit board, a microcontroller, or the like), the power source, and the heating element. These features may include at least two contacts on a bottom surface of the vaporizer cartridge 120 (referred to herein as cartridge contacts 124) and at least two contacts disposed near a base of the cartridge receptacle (referred to herein as receptacle contacts 125) of the vaporizer 100 such that the cartridge contacts 124 and the receptacle contacts 125 make electrical connections when the vaporizer cartridge 120 is inserted into and coupled with the cartridge receptacle 118. The circuit completed by these electrical connections can allow delivery of electrical current to the resistive heating element and may further be used for additional functions, such as for example for measuring a resistance of the resistive heating element for use in determining and/or controlling a temperature of the resistive heating element based on a thermal coefficient of resistivity of the resistive heating element, for identifying a cartridge based on one or more electrical characteristics of a resistive heating element or the other circuitry of the vaporizer cartridge, etc.

In some examples of the current subject matter, the at least two cartridge contacts and the at least two receptacle contacts can be configured to electrically connect in either of at least two orientations. In other words, one or more circuits necessary for operation of the vaporizer can be completed by insertion of a vaporizer cartridge 120 in the cartridge receptacle 118 in a first rotational orientation (around an axis along which the end of the vaporizer cartridge having the cartridge is inserted into the cartridge receptacle 118 of the vaporizer body 110) such that a first cartridge contact of the at least two cartridge contacts 124 is electrically connected to a first receptacle contact of the at least two receptacle contacts 125 and a second cartridge contact of the at least two cartridge contacts 124 is electrically connected to a second receptacle contact of the at least two receptacle contacts 125. Furthermore, the one or more circuits necessary for operation of the vaporizer can be completed by insertion of a vaporizer cartridge 120 in the cartridge receptacle 118 in a second rotational orientation such that the first cartridge contact of the at least two cartridge contacts 124 is electrically connected to the second receptacle contact of the at least two receptacle contacts 125 and the second cartridge contact of the at least two cartridge contacts 124 is electrically connected to the first receptacle contact of the at least two receptacle contacts 125. This feature of a vaporizer cartridge 120 being reversibly insertable into a cartridge receptacle 118 of the vaporizer body 110 is described further below.

In one example of an attachment structure for coupling a vaporizer cartridge 120 to a vaporizer body, the vaporizer body 110 includes a detent (e.g., a dimple, protrusion, etc.) protruding inwardly from an inner surface of the cartridge receptacle 118. One or more exterior surfaces of the vaporizer cartridge 120 can include corresponding recesses (not shown in FIG. 1A) that can fit and/or otherwise snap over such detents when an end of the vaporizer cartridge 120 inserted into the cartridge receptacle 118 on the vaporizer body 110. When the vaporizer cartridge 120 and the vaporizer body 110 are coupled (e.g., by insertion of an end of the vaporizer cartridge 120 into the cartridge receptacle 118 of the vaporizer body 110), the detent on the vaporizer body 110 may fit within and/or otherwise be held within the recesses of the vaporizer cartridge 120 to hold the vaporizer cartridge 120 in place when assembled. Such a detent-recess assembly can provide enough support to hold the vaporizer cartridge 120 in place to ensure good contact between the at least two cartridge contacts 124 and the at least two receptacle contacts 125, while allowing release of the vaporizer cartridge 120 from the vaporizer body 110 when a user pulls with reasonable force on the vaporizer cartridge 120 to disengage the vaporizer cartridge 120 from the cartridge receptacle 118.

Further to the discussion above about the electrical connections between a vaporizer cartridge and a vaporizer body being reversible such that at least two rotational orientations of the vaporizer cartridge in the cartridge receptacle are possible, in some vaporizers the shape of the vaporizer cartridge, or at least a shape of the end of the vaporizer cartridge that is configured for insertion into the cartridge receptacle may have rotational symmetry of at least order two. In other words, the vaporizer cartridge or at least the insertable end of the vaporizer cartridge may be symmetric upon a rotation of 180° around an axis along which the vaporizer cartridge is inserted into the cartridge receptacle. In such a configuration, the circuitry of the vaporizer may support identical operation regardless of which symmetrical orientation of the vaporizer cartridge occurs.

In some examples, the vaporizer cartridge, or at least an end of the vaporizer cartridge configured for insertion in the cartridge receptacle may have a non-circular cross section transverse to the axis along which the vaporizer cartridge is inserted into the cartridge receptacle. For example, the non-circular cross section may be approximately rectangular, approximately elliptical (e.g., have an approximately oval shape), non-rectangular but with two sets of parallel or approximately parallel opposing sides (e.g., having a parallelogram-like shape), or other shapes having rotational symmetry of at least order two. In this context, approximately having a shape, indicates that a basic likeness to the described shape is apparent, but that sides of the shape in question need not be completely linear and vertices need not be completely sharp. Rounding of both or either of edges or vertices of the cross-sectional shape is contemplated in the description of any non-circular cross section referred to herein.

The at least two cartridge contacts and the at least two receptacle contacts can take various forms. For example, one or both sets of contacts may include conductive pins, tabs, posts, receiving holes for pins or posts, or the like. Some types of contacts may include springs or other urging features to cause better physical and electrical contact between the contacts on the vaporizer cartridge and the vaporizer body. The electrical contacts may optionally be gold-plated, and/or can include other materials.

Figure 1B:
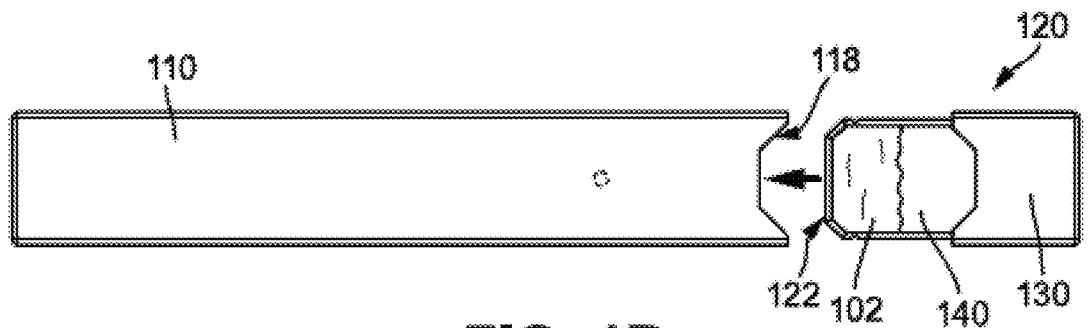
FIG. 1B illustrates a top view of the vaporizer of FIG. 1A, showing a cartridge separated from a vaporizer device body.

FIG. 1B illustrates an embodiment of the vaporizer device body 110 having a cartridge receptacle 118 into which the cartridge 120 may be releasably inserted. FIG. 1B shows a top view of the vaporization device 100 illustrating the cartridge being positioned for insertion into the vaporizer device body 110. Once inserted, a pod retention force must be overcome in order to release the cartridge 120 from the cartridge receptacle 118. When a user puffs on the vaporization device 100, air may pass between an outer surface of the cartridge 120 and an inner surface of a cartridge receptacle 118 on the vaporizer device body 110. Air can then be drawn into an insertable end 122 of the cartridge, through the vaporization chamber that includes or contains the heating element and wick, and out through an outlet of the mouthpiece 130 for delivery of the inhalable aerosol to a user. The reservoir 140 of the cartridge 120 may be formed in whole or in part from translucent material such that a level of vaporizable material 102 is visible along the cartridge 120.

Figure 1C:
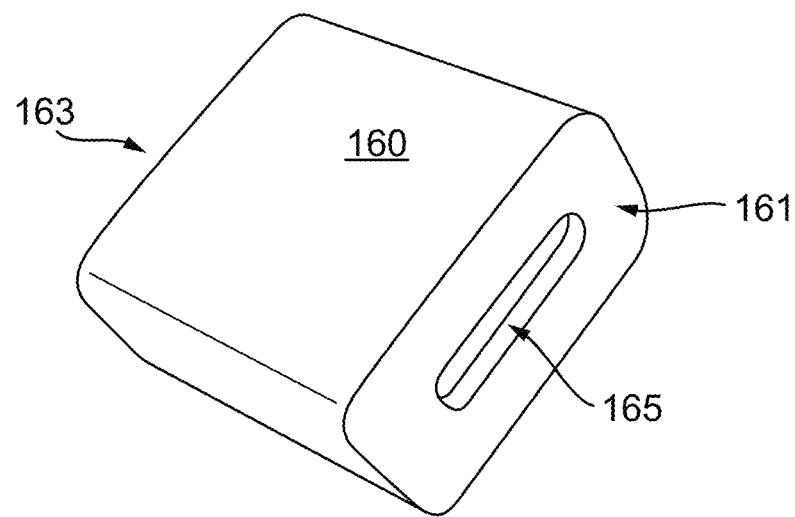
FIG. 1C is an isometric view of an outlet of a mouthpiece cover associated the with the vaporizer of FIG. 1A.

FIG. 1C is an isometric view of an outlet side 161 of a mouthpiece cover 160 associated with the vaporizer 100. The mouthpiece cover 160 also includes an inlet 163 at the distal end from the outlet 161 and a draw hole 165, which is one large hole relative to the size of outlet side 161, for vapor to pass through. The mouthpiece cover 160 can be made of silicone rubber. In general, silicone rubber is non-recyclable and non-biodegradable. Mouthpiece cover 160 can affect the vaporizer draw, reducing airflow and causing vapor to get trapped between the mouthpiece cover and pod. As such, the vaping experience with the mouthpiece cover 160 is not representative of the typical vaping experience with the vaporizer device 100. Most users consider and use the vaporizer device as a personal item and do not share the vaporizer device with others, and, therefore, simply use the vaporizer cartridge mouthpiece 120 to draw from and do not use the mouthpiece cover 160.

Figure 1D:
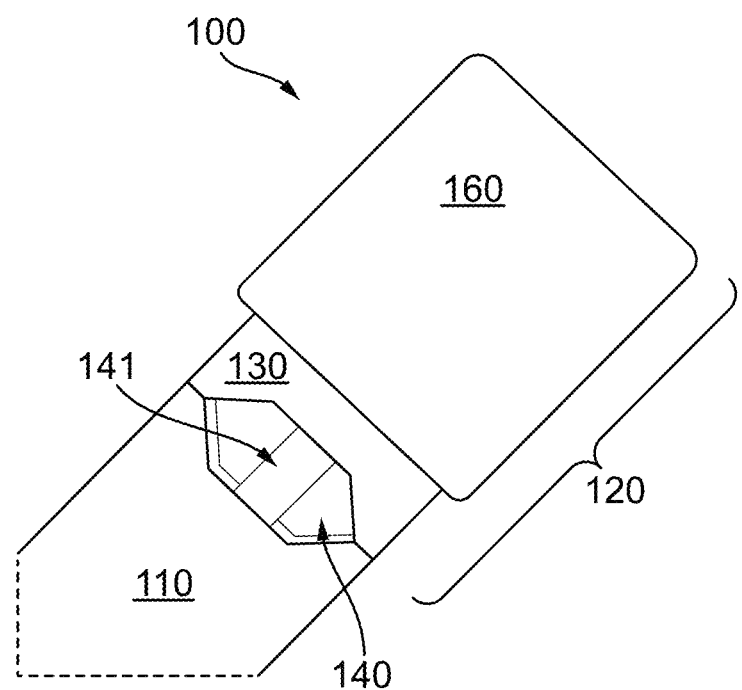
FIG. 1D is a partial top view of a mouthpiece cover mounted on the vaporizer of FIG. 1A.

FIG. 1D is a top view of the vaporizer 100 coupled to the mouthpiece cover 160, wherein the vaporizer cartridge 120 is inserted into the mouthpiece cover 160. As shown in FIG. 1D, mouthpiece cover 160 does not completely cover vaporizer cartridge mouthpiece 130, leaving a portion of vaporizer mouthpiece 130 proximate to reservoir 140 and atomizer 141 exposed. Once inserted, a mouthpiece cover retention force must be overcome in order to release the mouthpiece cover 160 from the cartridge mouthpiece 130. It is very difficult to remove the mouthpiece cover 160 from the cartridge mouthpiece 130. Because the mouthpiece cover retention force is high, users typically struggle for several minutes to remove the mouthpiece cover 160 from the cartridge mouthpiece 130. The difficulty in removing the mouthpiece cover 160 often leads to pod leakage and damage, because the pod generally gets stuck inside the cover, and the user must squeeze very tightly to remove the pod. This can result in pod leakage all over the user's hands.

Figure 2A:
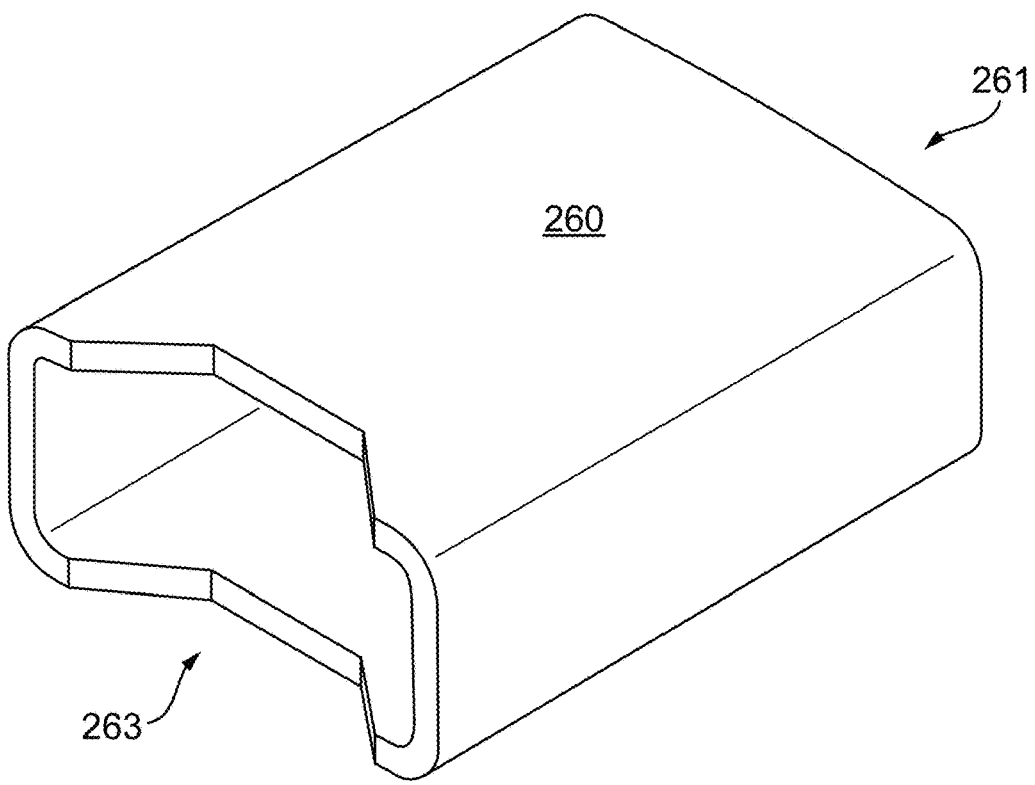
FIG. 2A is an isometric view of an inlet of an example embodiment of a vaporizer mouthpiece cover device in accordance with the implementations of the current subject matter.

FIG. 2A is an isometric view of an inlet 263 of an example embodiment of a vaporizer mouthpiece cover 260 in accordance with an implementation of the current subject matter. Arranged opposite of the inlet 263 of the vaporizer mouthpiece cover 260 is the outlet 261 at the distal end. The example embodiment of a mouthpiece cover 260 shown is FIG. 2A is generally a rounded rectangular tube shape.

Figure 2B:
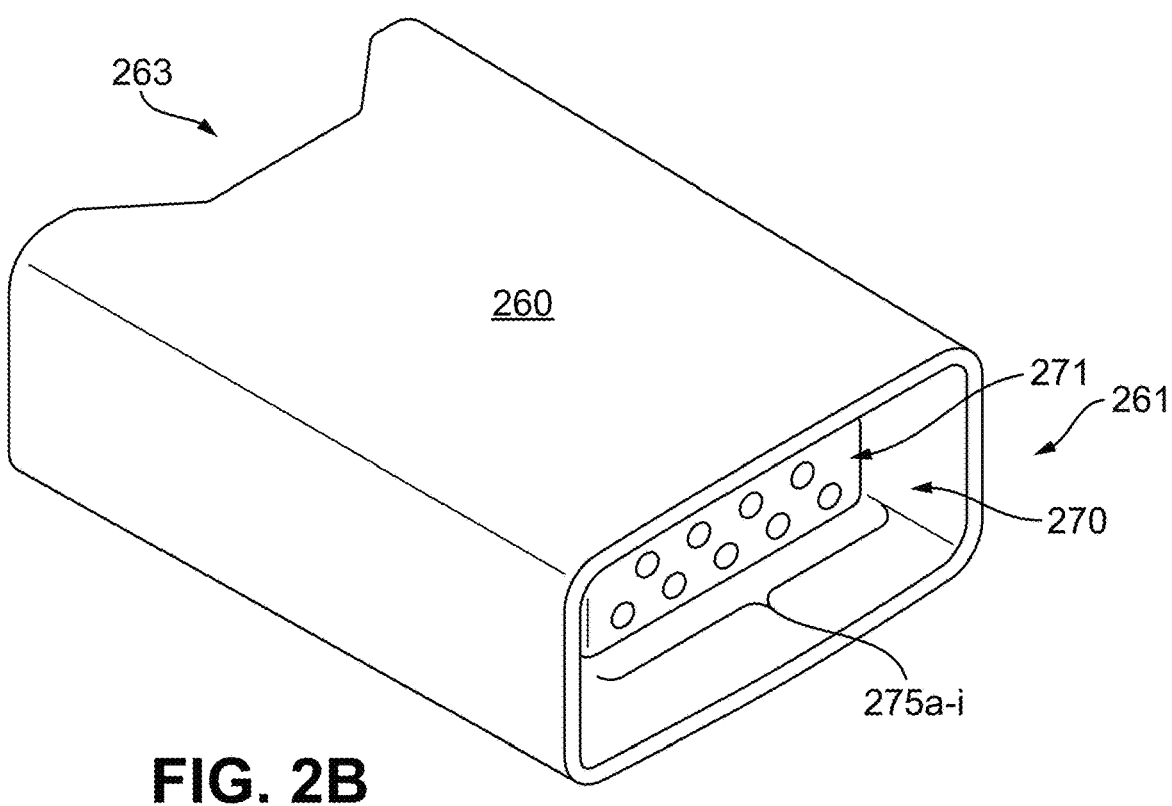
FIG. 2B is an isometric view of an outlet of an example embodiment of a vaporizer mouthpiece cover device in accordance with the implementations of the current subject matter.

FIG. 2B is an isometric view of the outlet 261 of an example embodiment of a vaporizer mouthpiece cover 260 in accordance with the implementations of the current subject matter. Arranged opposite of the outlet 261 of the vaporizer mouthpiece cover 260 is the inlet 263 at the distal end. Within the interior of mouthpiece cover 260 as shown within outlet 261 is saliva inhibitor 270. The saliva transfer inhibitor 270 includes a guard 271 with a number of draw holes 275a-i. In the example embodiment shown in FIG. 2B there are nine draw holes 275a-i.

The example embodiment of mouthpiece cover 260 does not significantly increase the restriction to a user's draw on the vaporizer 100, and, therefore, does not compromise the vaping experience. In other words, the use of mouthpiece cover 260 in a trial setting offers an experience truer to how a typical user will user the vaporizer 10. For the example embodiment of mouthpiece cover 260, the truer draw is achieved by nine approximately 0.8 mm diameter holes 275a-i. In other embodiments the draw holes 275a-i may have diameters between 0.7 mm and 0.9 mm inclusive. As those of skill in the art will appreciate, other quantities and size and shapes of draw holes are possible. The number and size of the draw holes enables vapor to pass through guard 271 while preventing user saliva from transfer into the pod. The table of test data below shows that the example embodiment of mouthpiece cover 260 adds only 2 millimeters per water column (mmwc) to the vaporizer system 100.

| Mouthpiece Cover Restriction to Draw Results | |
| --- | --- |
| Units = mmwc | Higher mmwc = more restriction |
| MP only | 2 |
| Pod only | 25 |
| MP + Pod | 26 |
| Pod + Device | 42 |
| MP + Pod + Device | 44 |

Figure 2C:
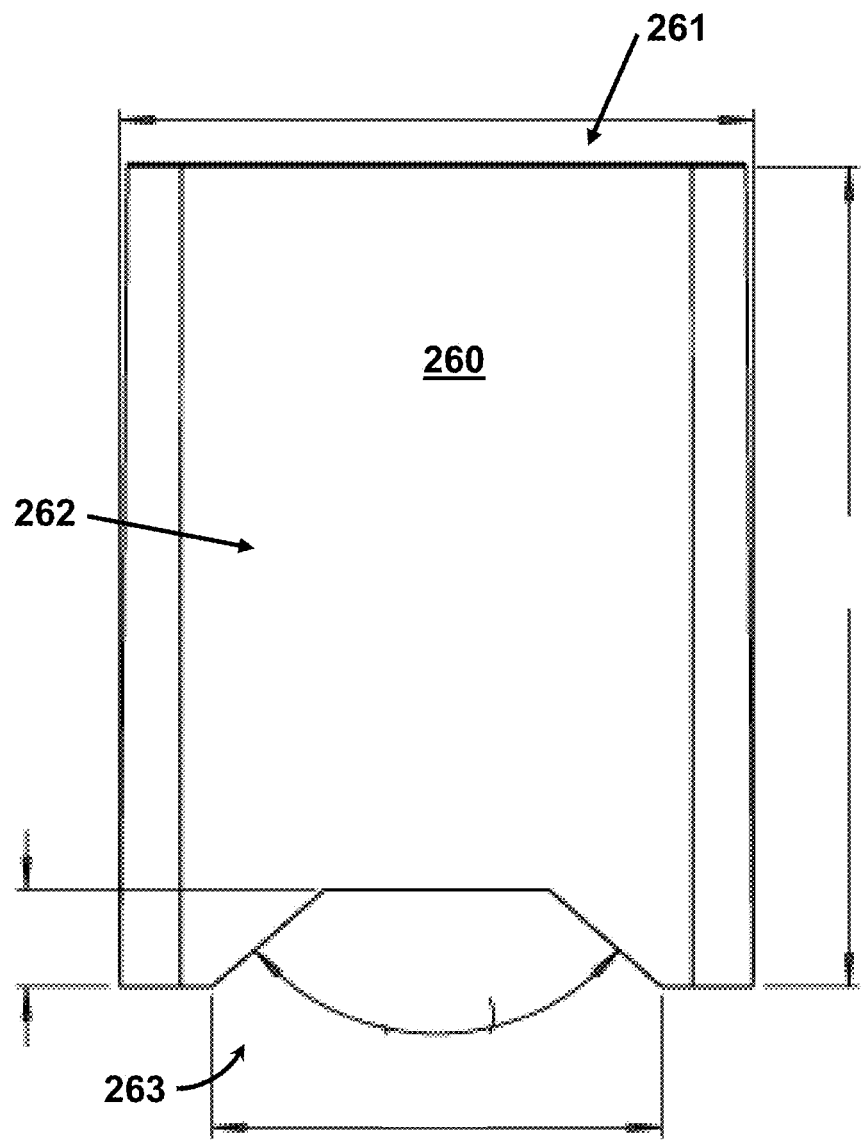
FIG. 2C is a top view of an example embodiment of a vaporizer mouthpiece cover device in accordance with the implementations of the current subject matter.

FIG. 2C is a top view of an example embodiment of the vaporizer mouthpiece cover 260 in accordance with the implementations of the current subject matter. The mouthpiece cover 260 includes an outlet 261 and an inlet 263. The inlet 263 is arranged opposite of the outlet 261 at the distal end of mouthpiece 260. The top view of the vaporizer mouthpiece cover 260 of FIG. 2C shows top face long side 262.

Figure 2D:
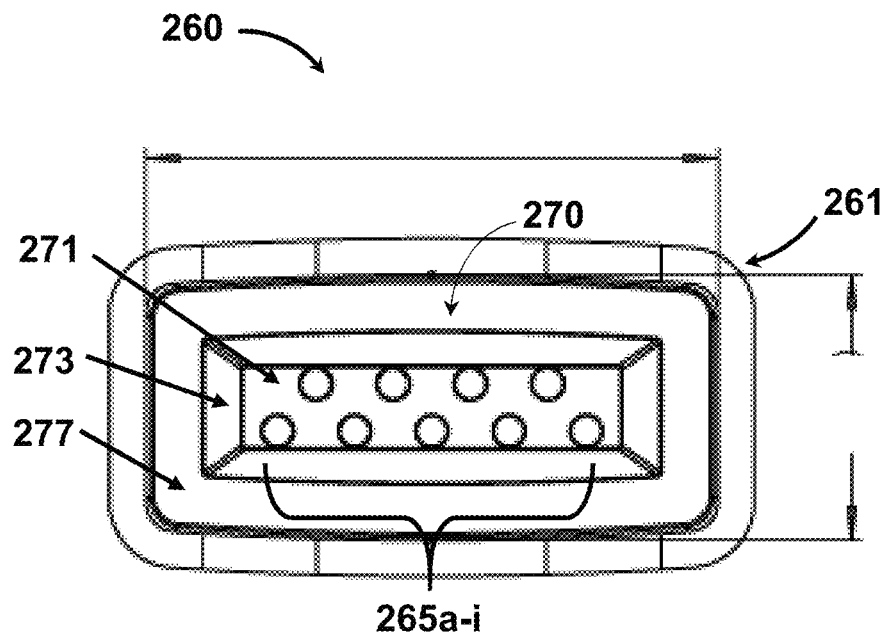
FIG. 2D is a side end view of an outlet of an example embodiment of a vaporizer mouthpiece cover device in accordance with the implementations of the current subject matter.

FIG. 2D is a side end view of an outlet 261 of an example embodiment of a vaporizer mouthpiece cover device 260 in accordance with the implementations of the current subject matter. As illustrated in FIG. 2D, mouthpiece cover 260 includes a saliva transfer inhibitor 270. The saliva transfer inhibitor 270 includes a guard 271 with draw holes 275a-i located therein. The example embodiment of the saliva transfer inhibitor 270 is generally shaped as a rectangular pyramidal frustum with guard sides 273. The base of rectangular pyramidal frustum saliva transfer inhibitor 270 is coupled to the interior of the rectangular tube mouthpiece cover 260 through a guard lip 277.

Figure 2E:
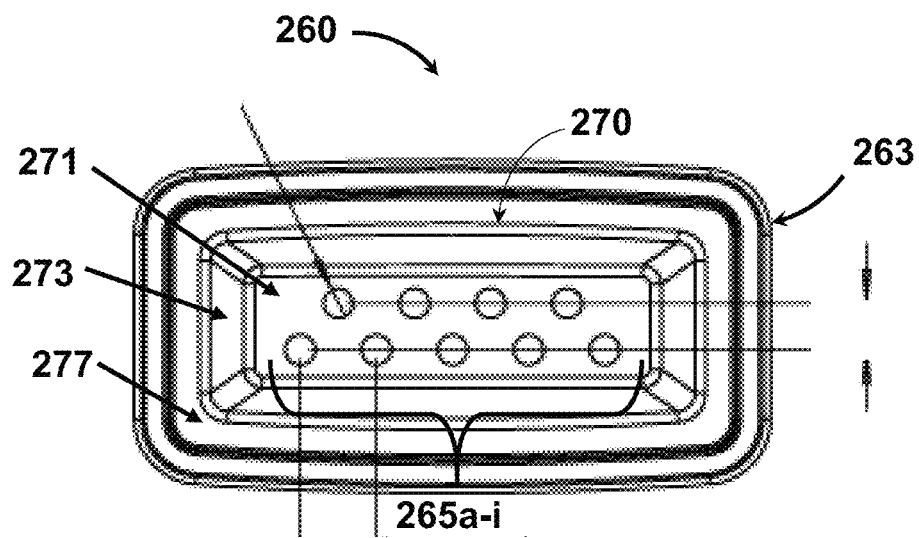
FIG. 2E is a side end view of an inlet of an example embodiment of a vaporizer mouthpiece cover device in accordance with the implementations of the current subject matter.

FIG. 2E is a side end view of an inlet 263 of an example embodiment of a vaporizer mouthpiece cover device 260 in accordance with the implementations of the current subject matter. As illustrated in FIG. 2E, mouthpiece cover 260 includes a saliva transfer inhibitor 270. The saliva transfer inhibitor 270 includes a guard 271 with draw holes 275a-i located therein. The example embodiment of the saliva transfer inhibitor 270 is generally shaped as a rectangular pyramidal frustum with guard sides 273. The base of rectangular pyramidal frustum saliva transfer inhibitor 270 is coupled to the interior of the rectangular tube mouthpiece cover 260 through a guard lip 277. Further, when the vaporizer cartridge 120 is inserted into mouthpiece cover 260 from the inlet 263, guard lip 277 acts as an obstruction, engaging with cartridge mouthpiece 120 and stopping cartridge 120 from further insertion into mouthpiece cover 260.

Figure 2F:
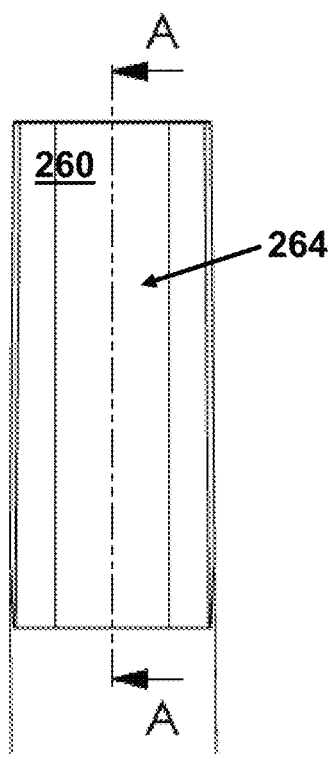
FIG. 2F is a side view of an example embodiment of a vaporizer mouthpiece cover device in accordance with the implementations of the current subject matter.

FIG. 2F is a side view of an example embodiment of a vaporizer mouthpiece cover device 260 in accordance with the implementations of the current subject matter. The side view of the vaporizer mouthpiece cover 260 of FIG. 2F shows side face short side 264. The short sides 264 of rounded rectangular tube-shaped vaporizer mouthpiece cover 260 are taller than long sides 262 (shown in FIG. 2C) and extend all the way over the mouthpiece 130 of cartridge 120.

Figure 2G:
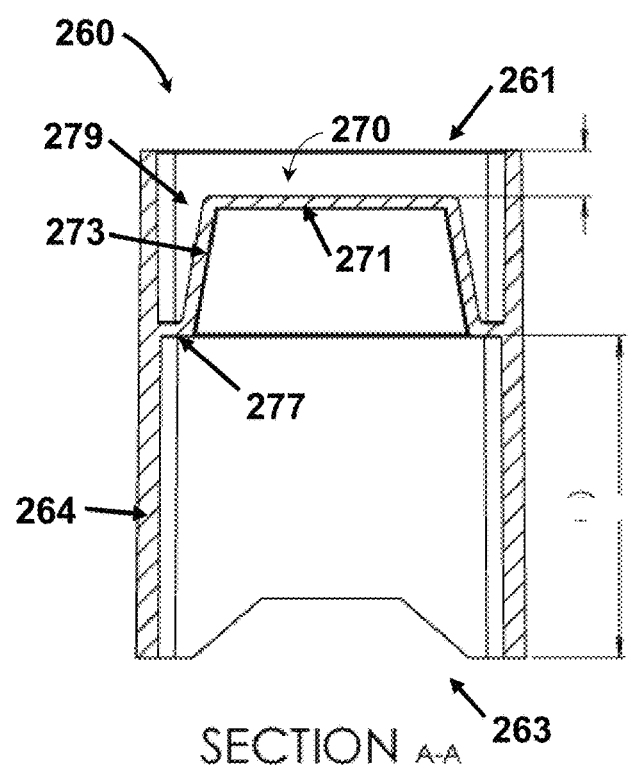
FIG. 2G is a cross-sectional view of an example embodiment of a vaporizer mouthpiece cover device of FIG. 2F at line A-A in accordance with the implementations of the current subject matter.

FIG. 2G is a cross-sectional view of an example embodiment of a vaporizer mouthpiece cover 260 of FIG. 2F at line A-A in accordance with the implementations of the current subject matter. As illustrated in FIG. 2G, mouthpiece cover 260 includes a saliva transfer inhibitor 270. The mouthpiece cover 260 and saliva transfer inhibitor 270 can be made from the same material, such as polypropylene, which is both a recyclable and biocompatible food-grade material, for example. Other recyclable and biocompatible food-grade material also can be used. The saliva transfer inhibitor 270 includes a guard 271. Although not shown in FIG. 2G, guard 271 includes draw holes, such as draw holes 275a-i of FIG. 2D, located therein. The example embodiment of the saliva transfer inhibitor 270 is generally shaped as a rectangular pyramidal frustum with guard sides 273. The base of rectangular pyramidal frustum saliva transfer inhibitor 270 is coupled to the interior of the rectangular tube mouthpiece cover 260 through a guard lip 277. The guard 271, guard walls 273, and guard lip 277 of saliva transfer inhibitor 270 in conjunction with the long sides 262 and short sides 264 define a void/form a saliva reservoir 279 at outlet 261. Further, when the vaporizer cartridge 120 is inserted into mouthpiece cover 260 from the inlet 263, guard lip 277 acts as an obstruction, engaging with cartridge mouthpiece 120 and stopping cartridge 120 from further insertion into mouthpiece cover 260.

FIGS. 3A and 3B illustrate the retention forces associated with the coupling of an example embodiment of a vaporizer mouthpiece cover 260 and a vaporizer device 100 in accordance with an implementation of the current subject matter. The fit of the mouthpiece cover 360 over the pod 120 is designed so that the mouthpiece cover 360 retention force is less than that of the pod retention force. The result of the mouthpiece cover 360 retention force being less than that of the pod retention force is that mouthpiece cover 360 can be removed easily without also removing the pod 120 from the device (e.g., from the cartridge receptacle 118 in vaporizer body 110 as shown in FIGS. 1A and 1B), and without causing pod 120 leakage or damage. The fit also enables the mouthpiece cover 360 to stay on securely, such that when only the mouthpiece cover 360 is held, the vaporizer body 110 still remains attached. Likewise, when only the vaporizer body 110 is held, the mouthpiece cover 360 remains attached.

The mouthpiece cover 360 is also designed so that the user can remove the mouthpiece cover and the pod 120 at the same time, by lightly pinching the long sides (e.g., longs sides 262 of FIG. 2C) upon removal. Simple removal through light pinching is achieved by offsetting the long sides of mouthpiece cover 360 by approximately 0.05 mm (or 0.04 to 0.06 mm) from the pod. This offset also enables the mouthpiece cover 360 to fit over pods 120 on the highest and lowest ends of a manufacturing tolerance range.

FIG. 4 is a further isometric view of an outlet 461 of an example embodiment of a vaporizer mouthpiece cover 460 in accordance with the implementations of the current subject matter. The vaporizer mouthpiece cover 460 includes an outlet 461, an inlet 463, has a generally rectangular tube shape with long side 462 and short side 464, where the long and short sides refer to the longer and shorter sides of the rectangle from which the tube protrudes. The mouthpiece cover 460 further includes a saliva transfer inhibitor 470. The saliva transfer inhibitor 470 is a structure arranged between the inlet 463 and the outlet 461 that includes a guard 471 having one or more draw holes 475a-i. The guard 471 in conjunction with the one or more draw holes 475a-i allow a user to draw vapor from the vaporizer 100 while inhibiting transfer of the user's saliva to the vaporizer 100, and more particularly the vaporizer cartridge mouthpiece 120.

FIGS. 5A and 5B are further cross-sectional views of an example embodiment of a vaporizer mouthpiece cover 560 in accordance with the implementations of the current subject matter and further illustrates the fit of the mouthpiece cover 560 over the vaporizer cartridge mouthpiece 120. FIG. 5A is a side cross-sectional view of the long side 562 of vaporizer mouthpiece cover 560. FIG. 5B is a side cross-sectional view of the short side 564 of vaporizer mouthpiece cover 560. The vaporizer mouthpiece cover 560 includes an outlet 561, inlet 563, longer side 562, shorter side 564, and saliva transfer inhibitor 570. In FIGS. 5A and 5B, mouthpiece cover 560 is shown with vaporizer cartridge 120 inserted therein. The mouthpiece cover 560 sheathes the entire pod mouthpiece 130, providing complete coverage and protection. The full coverage provided by the mouthpiece cover 560 fitting over the entire pod mouthpiece 130 provides increased sanitation.

The example embodiment of the saliva transfer inhibitor 570 shown in FIGS. 5A and 5B is located between the inlet 563 and outlet 561 of the mouthpiece cover 560 and offset closer to the outlet 561. The saliva transfer inhibitor 570 includes guard 571, provides a physical barrier between the inlet 563 and outlet 561, and is generally a rounded rectangular pyramidal frustum with sides 573, a base open to inlet 563, and a lip 577 coupling the base of the rectangular pyramidal frustum with rounded rectangular pyramidal frustum with the interior sides (e.g., long sides 562 and short sides 564) of mouthpiece cover 560. The lip 577 coupling the mouthpiece cover 560 and saliva transfer inhibitor 570 can be a tight seal. Alternatively, the mouthpiece cover 560 and saliva transfer inhibitor 570 can be made together and formed from the same mold, for example, from a recyclable and biodegradable material such as food grade polypropylene.

The cavity defined by and between the outlet 561 and saliva transfer inhibitor 570 acts as a reservoir 579 and inhibits a user's saliva from traveling beyond the saliva inhibitor 570 to the pod mouthpiece 130. While the guard 571 of the saliva inhibitor 570 provides a physical barrier between the inlet 563 and outlet 561 to block saliva transfer, the guard also includes one or more draw holes 575 configured to allow a user an unrestricted vapor draw from the mouthpiece 130 of the vaporizer device 100.

Figure 6:
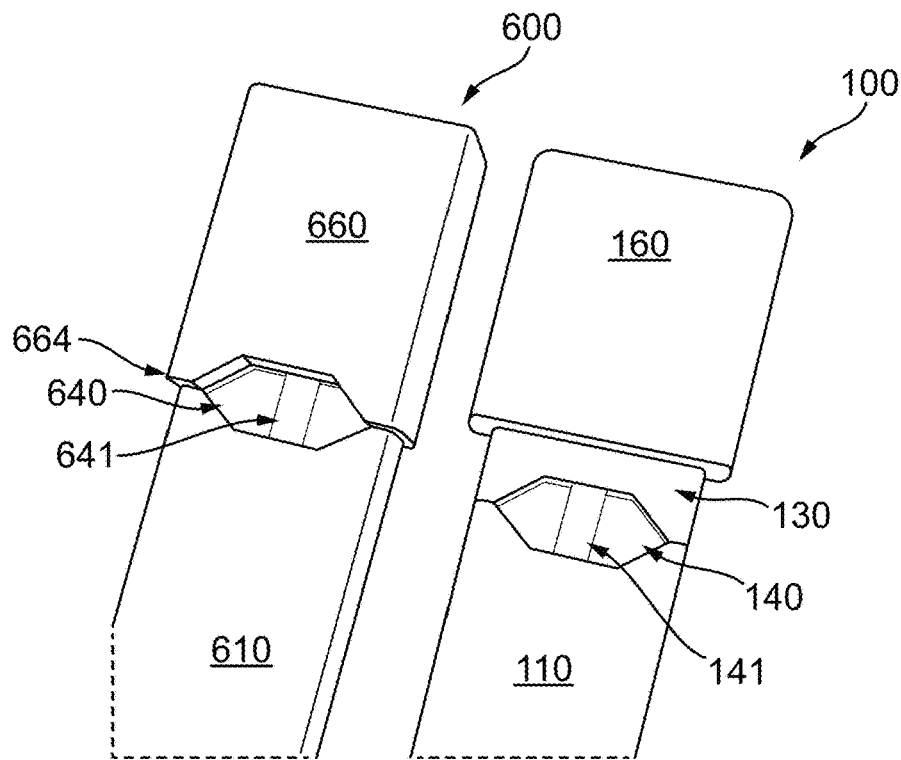
FIG. 6 is an illustration of an example embodiment of a vaporizer mouthpiece cover device in accordance with the implementations of the current subject matter.

FIG. 6 is an illustration comparing the mouthpiece cover 160 and an example embodiment of a vaporizer mouthpiece cover 660 in accordance with the implementations of the current subject matter. Vaporizer device 100 includes a vaporizer body 110, vaporizer cartridge, of which the atomizer 141, vaporizable material reservoir 140, and pod mouthpiece 130 are shown, and is inserted into mouthpiece cover 160. Mouthpiece cover 160 does not fully cover pod mouthpiece 130. The vaporizer device 600 includes a vaporizer body 610, vaporizer cartridge, of which only the atomizer 641 and vaporizable material reservoir 640 are visible, and is inserted into an example embodiment mouthpiece cover 660. The example embodiment of mouthpiece cover 660 completely covers the pod mouthpiece (e.g., pod mouthpiece 130), leaving only the vaporizable material reservoir 640 and atomizer 641 exposed. Because the pod mouthpiece is completely covered, example embodiment mouthpiece cover 660 provides increased sanitation.

Figure 7:
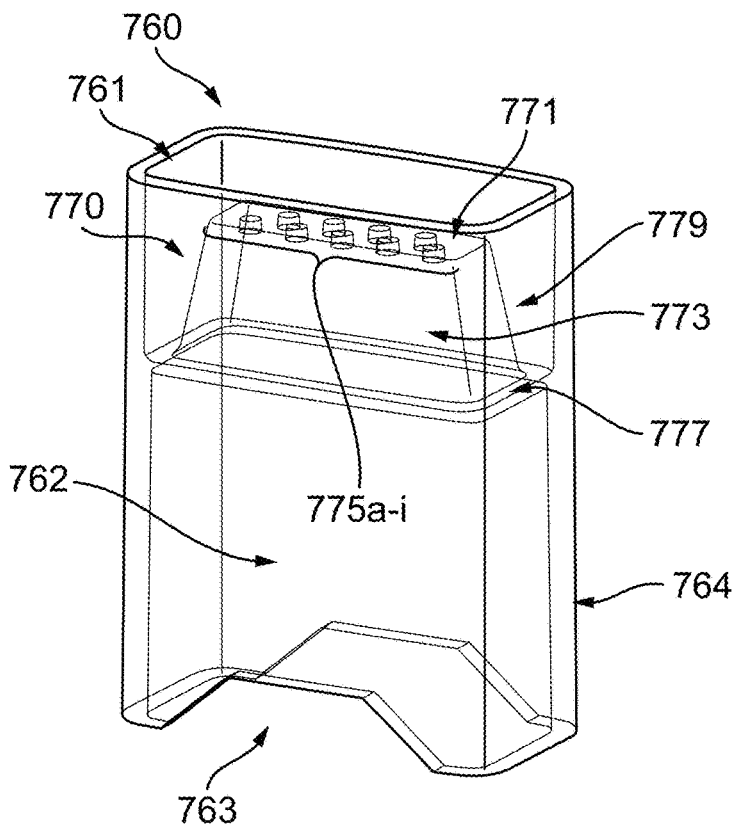
FIG. 7 is a transparent perspective view of an example embodiment of a vaporizer mouthpiece cover device in accordance with the implementations of the current subject matter.

FIG. 7 is a transparent perspective view of an example embodiment of a vaporizer mouthpiece cover 760 in accordance with the implementations of the current subject matter. The vaporizer mouthpiece cover 760 includes an outlet 761, inlet 763, longer side 762, shorter side 764, and saliva transfer inhibitor 570. Longer sides 762 include a notch cutout that exposes the vaporizable material reservoir and atomizer of a vaporizer pod. As such, shorter sides 764 are generally taller than longer sides 762.

The example embodiment of the saliva transfer inhibitor 770 shown in FIG. 7 is located between the inlet 763 and outlet 761 of the mouthpiece cover 760 and offset closer to the outlet 761. The saliva transfer inhibitor 770 includes guard 771, provides a physical barrier between the inlet 763 and outlet 761, and is generally a rounded rectangular pyramidal frustum with sides 773, a base open to inlet 763, and a lip 777 coupling the base of the rectangular pyramidal frustum with rounded rectangular pyramidal frustum with the interior sides (e.g., long sides 762 and short sides 764) of mouthpiece cover 760. The lip 777 coupling the mouthpiece cover 760 and saliva transfer inhibitor 770 can provide a tight seal between the two.

In some embodiments, the mouthpiece cover 760 and saliva transfer inhibitor 770 can be made together and formed from the same mold, for example, from a recyclable and biodegradable material such as food grade polypropylene, so that the saliva transfer inhibitor 770 is an integral part of the mouthpiece cover 760 as a monolithic piece. As shown in FIG. 7, a cavity area (e.g., an alley) may be defined by and between the outlet 761 and saliva transfer inhibitor 770 to act as a reservoir 779 and collect and inhibit a user's saliva from traveling beyond the saliva inhibitor 770 to a pod mouthpiece. While the guard 771 of the saliva inhibitor 770 provides a physical barrier between the inlet 763 and outlet 761 to block saliva transfer, the guard also includes one or more (e.g., nine (9)) draw holes 775*a-i* configured to allow a user an unrestricted (e.g., an increase in restriction of 2 mmwc or less) vapor draw from the mouthpiece of the vaporizer device. Those of skill in the art ill recognize that other configurations are possible and within the scope of the implementations presented herein.

Terminology

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present.

Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments and implementations only and is not intended to be limiting. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

Spatially relative terms, such as "forward", "rearward", "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings provided herein.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the teachings herein. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the claims.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

Any admissions, amendments, characterizations, or other assertions made, previously or going forward, in any related patent applications or patents (including any continuation or continuation-in-part applications or any parent, sibling, or child applications) with respect to any art, prior or otherwise, should not be construed as a disclaimer of any subject matter supported by the disclosure made in the present application. Applicant hereby rescinds and retracts any disclaimers or admissions whatsoever made in any related applications or patents during prosecution or otherwise. Applicant also respectfully submits that any prior art considered in any related patent applications or patents may need to be re-visited and reconsidered as to relevance and applicability to the subject matter disclosed and claimed herein.

What is claimed is:

1. A mouthpiece cover for a vaporizer device, the mouthpiece cover comprising:
    an outlet for vapor to exit the vaporizer device; and
    an inlet arranged at a distal end from the outlet and configured to sheathe a vaporizer cartridge mouthpiece, the vaporizer cartridge mouthpiece held within the mouthpiece cover by a first retention force and a vaporizer cartridge held within a vaporizer cartridge receptacle by a second retention force, wherein the first retention force is less than the second retention force;
    a guard arranged between the outlet and the inlet and configured to obstruct the vaporizer cartridge mouthpiece from coupling to the outlet; and
    a reservoir for capturing saliva, the reservoir defined by a void between the outlet and the guard.

2. The mouthpiece cover of claim 1, wherein the mouthpiece cover is made from a recyclable material.

3. The mouthpiece cover of claim 1, wherein the mouthpiece cover is made from a food grade material.

4. The mouthpiece cover of claim 1, wherein the mouthpiece cover is made from a biocompatible material.

5. The mouthpiece cover of claim 1, wherein the mouthpiece cover is arranged as a generally rounded rectangular tube having two longs sides and two short sides, wherein the long sides are in an offset arrangement with the vaporizer cartridge mouthpiece.

6. The mouthpiece cover of claim 1, wherein one or more draw holes are formed in the guard for vapor to pass through the guard.

7. The mouthpiece cover of claim 6, wherein nine draw holes are formed in the guard for vapor to pass through the guard.

8. The mouthpiece cover of claim 1, wherein the guard is further arranged as a generally rectangular pyramidal frustum having the bottom open to the vaporizer cartridge mouthpiece and the top proximate to the outlet.

9. A vaporizer device accessory comprising:
    a body having a hollow interior to fit over a mouthpiece of a vaporizer device, the body comprising:
        an outlet on a first side of the body;
        an inlet on a second side of the body opposite to the outlet, the inlet having been formed to receive therein a distal end of the mouthpiece; and
        a saliva transfer inhibitor comprising a guard having one or more holes positioned between the outlet and the inlet, the saliva transfer inhibitor shaped as a pyramidal frustum.

10. The vaporizer device accessory of claim 9, wherein a base of the pyramidal frustum is coupled to an interior of the rectangular tube mouthpiece cover through a guard lip.

11. The vaporizer device accessory of claim 10, wherein the base of the pyramidal frustum is substantially rectangular in shape.

12. The vaporizer device accessory of claim 10, wherein the guard lip acts as an obstruction, engaging with a mouthpiece portion of the vaporizer device cartridge to stop the cartridge from insertion into the body beyond a first threshold.

13. The vaporizer device accessory of claim 9, wherein the mouthpiece is held within the body by a first retention force and a vaporizer cartridge attached to the mouthpiece is held within a vaporizer cartridge receptacle by a second retention force.

14. The vaporizer device accessory of claim 13, wherein the first retention force is less than the second retention force.

15. The vaporizer device accessory of claim 13, wherein the vaporizer cartridge is removable from the vaporizer cartridge receptacle with the mouthpiece being held within the body, in response to a pinching force applied externally to at least two sides of the body of the vaporizer device accessory.

16. The vaporizer device accessory of claim 15, wherein the at least two sides are internally offset from corresponding two external sides of the mouthpiece.

17. The vaporizer device accessory of claim 16, wherein at least one of the two sides is offset by approximately 0.04 to 0.06 mm from a corresponding external side of the mouthpiece.

18. A vaporizer device, comprising:
    a vaporizer body having a cartridge receptacle;
    a vaporizer cartridge configured to be inserted into the cartridge receptacle, the cartridge having a vaporizer cartridge mouthpiece; and
    a mouthpiece cover having an outlet for vapor to exit the vaporizer device, and an inlet arranged at a distal end from the outlet, the mouthpiece cover configured to sheathe the vaporizer cartridge mouthpiece, wherein the vaporizer cartridge mouthpiece is held within the mouthpiece cover by a first retention force and the vaporizer cartridge is held within the cartridge receptacle by a second retention force, wherein the first retention force is less than the second retention force.

19. The vaporizer device of claim 18, wherein the mouthpiece cover is arranged as a generally rounded rectangular tube having two longs sides and two short sides, wherein the long sides are in an offset arrangement with the vaporizer cartridge mouthpiece.

20. The vaporizer device of claim 19, wherein the two short sides are taller than the two long sides, wherein the two short sides extend over the vaporizer cartridge mouthpiece of the vaporizer cartridge.

* * * * *